(12) United States Patent
Slagle (10) Patent No.: US 10,172,646 B2
(45) Date of Patent: Jan. 8, 2019

(54) SURGICAL CLAMPS

(71) Applicant: Biomet Manufacturing, LLC, Warsaw, IN (US)

(72) Inventor: Paul Thomas Slagle, Leesburg, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/991,257

(22) Filed: Jan. 8, 2016

(65) Prior Publication Data
US 2016/0199098 A1   Jul. 14, 2016

Related U.S. Application Data

(60) Provisional application No. 62/101,681, filed on Jan. 9, 2015, provisional application No. 62/101,696, filed on Jan. 9, 2015.

(51) Int. Cl.
| | | |
|---|---|---|
| *A61B 17/66* | (2006.01) | |
| *A61B 17/64* | (2006.01) | |
| *A61B 17/60* | (2006.01) | |

(52) U.S. Cl.
CPC .......... *A61B 17/6458* (2013.01); *A61B 17/60* (2013.01); *A61B 17/645* (2013.01); *A61B 17/6466* (2013.01)

(58) Field of Classification Search
CPC ..... A61B 17/66; A61B 17/62; A61B 17/6466; A61B 17/6416; A61B 17/645; A61B 17/6458; A61B 17/6441; A61B 17/6475
USPC .................................................... 606/53–59
See application file for complete search history.

(56) References Cited

U.S. PATENT DOCUMENTS

| | | | | |
|---|---|---|---|---|
| 5,020,195 A | * | 6/1991 | LeVahn | A61B 17/02 24/514 |
| 5,803,924 A | * | 9/1998 | Oni | A61B 17/6416 606/54 |
| 5,888,197 A | * | 3/1999 | Mulac | A61B 17/02 403/396 |

(Continued)

FOREIGN PATENT DOCUMENTS

| | | |
|---|---|---|
| CN | 107427316 A | 12/2017 |
| EP | 0972491 A1 | 1/2000 |
| WO | WO-2016112281 A1 | 7/2016 |

OTHER PUBLICATIONS

"International Application Serial No. PCT/US2016/012633, International Search Report dated Apr. 14, 2016", 5 pgs.

(Continued)

*Primary Examiner* — Eduardo C Robert
*Assistant Examiner* — Tara R Carter
(74) *Attorney, Agent, or Firm* — Schwegman Lundberg & Woessner, P.A.

(57) ABSTRACT

The present disclosure provides a clamp. The clamp can include a first clamp member, a second clamp member, and a lever. The first clamp member can include a first gripping surface. The second clamp member can include a second gripping surface. The lever can be connected to the first clamp member and can define a cam located proximate the first clamp member. The lever can be pivotable between a first position and a second position. A transition from the first position to the second position can cause the cam to move the second clamp member towards the first clamp member.

12 Claims, 5 Drawing Sheets

(56) References Cited

U.S. PATENT DOCUMENTS

| | | | |
|---|---|---|---|
| 5,897,087 A | 4/1999 | Farley | |
| 7,314,331 B1* | 1/2008 | Koros | A61B 90/50 403/385 |
| 2002/0077629 A1 | 6/2002 | Hoffman et al. | |
| 2009/0306661 A1* | 12/2009 | Thomke | A61B 17/645 606/54 |
| 2012/0203225 A1* | 8/2012 | Mingozzi | A61B 17/6466 606/59 |
| 2014/0276816 A1 | 9/2014 | Cresina et al. | |

OTHER PUBLICATIONS

"International Application Serial No. PCT/US2016/012633, Written Opinion dated Apr. 14, 2016", 5 pgs.

"European Application Serial No. 16701891.0, Reponse filed Mar. 13, 2018 to Office Action dated Sep. 5, 2018", 15 pgs.

"International Application Serial No. PCT/US2016/012633, International Preliminary Report on Patentability dated Jul. 20, 2017", 7 pgs.

* cited by examiner

SURGICAL CLAMPS

RELATED APPLICATIONS

This application claims the benefit of priority to U.S. Provisional Application Ser. No. 62/101,681, filed Jan. 9, 2015 and U.S. Provisional Application Ser. No. 62/101,969, filed Jan. 9, 2015, the contents of which are hereby incorporated by reference in their entireties.

FIELD OF THE DISCLOSURE

The present disclosure relates to surgical instruments. More specifically, the present disclosure relates to surgical clamps that can be used during and after surgical procedures.

BACKGROUND

Traditional surgical clamps utilize a screw mechanism that can require use of a wrench or other tools to secure the clamp. The additional tools can cause increased complexity. Furthermore, traditional clamps can cause damage to the rods, pins, and wires due to overtightening of the screw mechanism.

SUMMARY

To better illustrate the clamp disclosed herein, a non-limiting list of examples is provided here:

In Example 1, a clamp can comprise a first clamp member, a second clamp member, and a lever. The first clamp member can include a first gripping surface. The second clamp member can include a second gripping surface. The lever can be connected to the first clamp member. The lever can define a cam located proximate the first clamp member. The lever can be pivotable between a first position and a second position. A transition from the first position to the second position can cause the cam to move the second clamp member towards the first clamp member.

In Example 2, the clamp of Example 1 can optionally include a head that can connect the lever to the first clamp. The head can provide a pivot axis about which the lever can pivot.

In Example 3, the clamp of Example 2 can optionally include the head defining a recess and the lever defining a locking hole. When the lever is in the second position, the locking hole can be aligned with the recess.

In Example 4, the clamp of Example 3 can optionally include a locking in sized to fit into the locking hole and the recess.

In Example 5, the clamp of any one of or any combination of Examples 1-4 can optionally include the lever being pivotable at least 180 degrees.

In Example 6, the clamp of any one of or any combination of Examples 1-5 can optionally include the first gripping surface defining a notch sized to receive a predetermined gauge wire.

In Example 7, the clamp of any one of or any combination of Examples 1-6 can optionally include the first clamp member or the second clamp member including a textured surface.

In Example 8, the clamp of any one of or any combination of Examples 1-7 can optionally include the first gripping surface and the second gripping surface exerting a predetermined gripping force when the lever is in the second position.

In Example 9, the clamp of any one of or any combination of Examples 1-8 can optionally include a second clamp connected to the clamp.

In Example 10, the clamp of any one of or any combination of Examples 1-8 can optionally include a rotational joint connecting the clamp to a second clamp.

In Example 11, the clamp of Example 10 can optionally include the rotational joint allowing the second clamp to rotate independently of the clamp.

In Example 12, the clamp of any one of or any combination of Examples 9-11 can optionally include the second clamp including a third gripping surface defined by the first clamp member and a fourth gripping surface defined by the second clamp member.

In Example 13, the clamp of any one of or any combination of Examples 9-12 can optionally include the second clamp including a second lever identical to the lever.

In Example 14, the clamp of any one of or any combination of Examples 9-13 can optionally include the clamp being sized to grip a first wire and the second clamp being sized to grip a second wire. The first wire and the second wire can be of different gauges.

In Example 15, the clamp of any one of or any combination of Examples 1-14 can optionally include the lever including a textured surface.

In Example 16, the clamp of any one of or any combination of Examples 1-14 can optionally include the cam including a textured surface.

In Example 17, a damp can include a first clamping member, a second clamping member, and a plurality of levers. The first clamping member can include a first plurality of gripping surfaces. The second clamping member can include a second plurality of gripping surfaces. The plurality of levers can be connected to the first clamping member. Each of the levers can include a cam pivotable between a first position and a second position. A transition from the first position to the second position can cause the cam to move a portion of the second clamping member towards a portion of the first clamping member.

In Example 18, the clamp of Example 17 can optionally include a plurality of heads. Each of the plurality of heads can connect a corresponding lever to the first clamp member. Each of the plurality of heads can provide a pivot axis about which the corresponding lever can pivot.

In Example 19, the clamp of Example 18 can optionally include each of the heads defining a recess and each of the levers defining a locking hole. A corresponding locking hole can be aligned with a corresponding recess when each of the levers is in the second position.

In Example 20, the clamp of Example 19 can optionally include a plurality of locking pins sized to fit into the locking holes and the recesses.

In Example 21, the clamp of any one of or any combination of Examples 17-20 can optionally include each of the levers being pivotable at least 180 degrees.

In Example 22, the clamp of any one of or any combination of Examples 17-21 can optionally include one of the plurality of gripping surfaces defining a notch sized to receive a predetermined gauge wire.

In Example 23, the clamp of any one of or any combination of Examples 17-22 can optionally include the first plurality of gripping surfaces or the second plurality of gripping surfaces including a textured surface.

In Example 24, the clamp of any one of or any combination of Examples 17-23 can optionally include the first gripping surface and the second gripping surface exerting a predetermined gripping force when the plurality of levers are in the second position.

In Example 25, the clamp of any one of or any combination of Examples 17-24 can optionally include each of the plurality of levers including a textured surface.

In Example 26, the clamp of any one of or any combination of Examples 17-24 can optionally include each of the cams including a textured surface.

In Example 27, a clamping system can comprise a plurality of rods, wires, or pins and a plurality of clamps. Each of the plurality of clamps can include a first clamp member, a second clamp member, and a lever. The first clamp member can include a first gripping surface. The second clamp member can include a second gripping surface. The lever can connect to the first clamp member. The lever can define a cam located proximate the first clamp member. The lever can be pivotable between a first position and a second position. A transition from the first position to the second position can cause the cam to move the second clamp member towards the first clamp member. Each of the plurality of clamps can be sized to clamp onto at least one of the plurality of rods, wires, or pins.

In Example 28, the clamping system of Example 27 can optionally include at least one of the plurality of clamps being sized to clamp onto at least two of the plurality of rods, wires, or pins.

In Example 29, the clamping system of any one of or any combination of Examples 27 and 28 can optionally include each of the plurality of rods, wires, or pins being of different gauges.

In Example 30, the clamping system of any one of or any combination of Examples 27-29 can optionally include a curved support. At least one of the plurality of clamps can be sized to connect to the curved support.

In Example 31, the clamp or clamping system of any one of or any combination of Examples 1-30 can optionally be configured such that all elements or options recited are available to use or select from.

BRIEF DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention any manner.

DETAILED DESCRIPTION

During and after a surgical procedure various rods, pins, and wires may need to be clamped into position. As disclosed herein, clamps can utilize a cam to cause clamping members, sometimes referred to as jaws or clamping surfaces to grip or otherwise constrain rods, pins, or wires. In addition, the cam can be used to cause the clamping members to grip a fixture, such as a support used in realignment procedures or to support bones or other limbs after a compound fracture.

Clamps disclosed herein can utilize a cam to lock an element into position. For example upon placing a rod proximate a support structure, a lever can be pivoted from a first position to a second position. During the pivoting action, the cam can cause the clamping surfaces of the clamp to come together and grip the rod, pin, wire, or support structure.

As disclosed herein, a locking pin in conjunction with locking holes and recesses can be used to secure the lever in a locked position. Furthermore, the cam can include a textured surface that can be used to secure the lever in a locked position. The clamps can exert a predetermined gripping force on rods, pins, wires, and support structures. For example, when in a clamped position, the clamps can exert gipping force strong enough to support a 150 kg mass (approximately 330 lbs).

As disclosed herein, a clamp can include a single clamp or multiple clamps. The multiple clamps can be connected together using rotational joints that allow the individual clamps to rotate independent of one another. In addition, elongated materials can form the jaws of a clamp and multiple levers can be used to cause the jaws to close.

Figure 1:
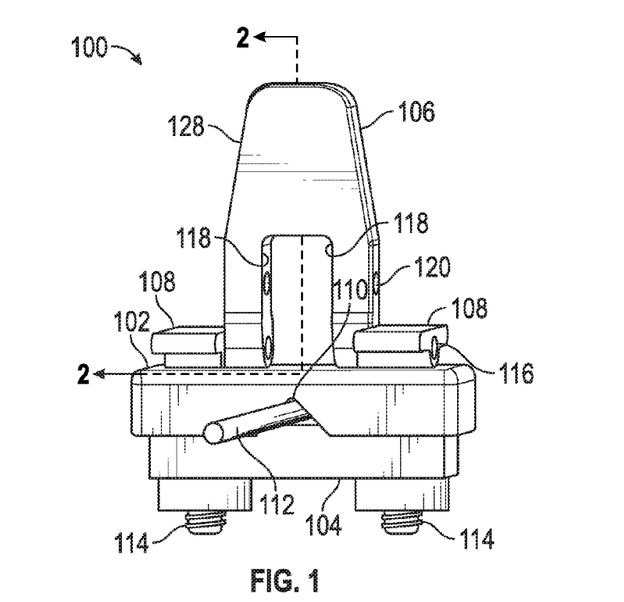
FIG. 1 shows an example of a clamp consistent with embodiments disclosed herein.

Referring now to the figures, FIG. 1 shows a clamp 100. The clamp 100 can include a clamp member 102, a clamp member 104, a lever 106, and one or more heads 108 (also referred to herein as "heads 108"). The clamp member 102 can include a gripping surface that defines a notch 110 that can receive a wire 112. While FIG. 1 shows the notch 110 defined by the gripping surface of the clamp member 102, the notch 110 can also be defined by a gripping surface of the clamp member 104.

Figure 2A:
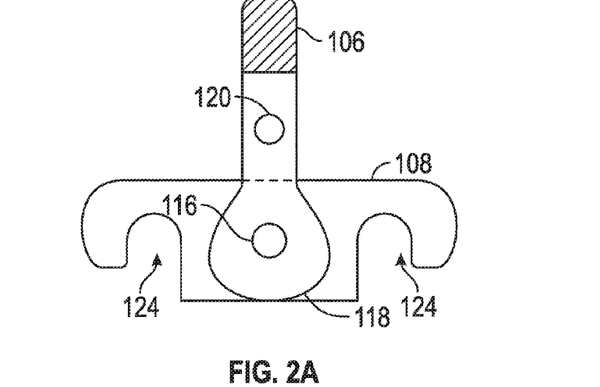
FIGS. 2A and 2B show a lever in a first position and a second position, respectively, consistent with embodiments disclosed herein.
Figure 2B:
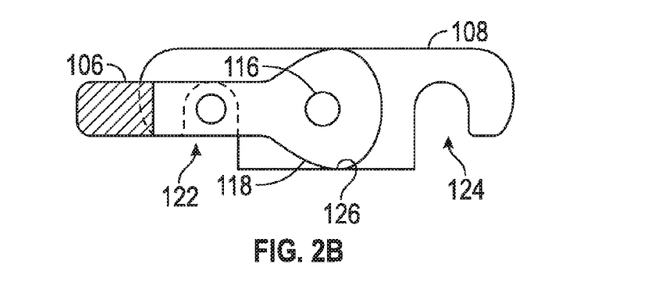

The heads 108 can be a portion of a bolt or a structure that is attached to the clamp member 102. For example, the heads 108 can be a machined metal that is attached to the clamp member 102 with an adhesive, welded to the clamp member 102, or bolted to the clamp member 102 with bolts 114. The heads 108 can provide a pivot axis 116 about which the lever 106 can pivot. As shown in FIGS. 2A and 2B, the lever 106 can define a cam 118 and a locking hole 120. While the lever 106 is in a first position (FIG. 2A) the clamp member 102 and the clamp member 104 are spaced apart a first distance. As the lever 106 transitions to a second position (FIG. 2B) the cam 118 can cause the clamp member 104 to approach the clamp member 102 such that the clamp member 102 and the clamp member 104 are spaced a second distance apart. The second distance can be shorter than the first distance. Stated another way, the transition from the first position to the second position can cause the clamp 100 to close and grip the wire 112.

To assist in keeping the lever 106 in the second position, a locking pin 122 can pass underneath a portion of the heads 108 and rest in a recess 124 on either side of the heads 108. In addition, the locking pin 122 can pass through the locking hole 120 defined by the lever 106, Furthermore, the cam 118 can have a textured surface 126 that increases friction between the cam 118 and a bearing surface, such as the clamp member 102, to assist in maintaining a position of the lever 106. In addition, the lever 106 can have a textured surface 128 to assist a surgeon in gripping the lever 106.

As shown in FIGS. 2A and 2B, the recess 124 can be formed on both sides of the head 108. The lever 106 can pivot 180 degrees to utilize both recesses 124. In addition, the cam 118 can have two different profiles. For example, pivoting the lever 106 in a first direction (e.g., counterclockwise) can cause the distance between the clamp member 102 and the clamp member 104 to be X and pivoting the lever 106 in a second direction (e.g., clockwise can cause the distance between the clamp member 102 and the clamp member 104 to be Y where X is greater than Y.

The clamp 100 can be manufactured from a variety of materials and using a variety of manufacturing techniques. For example, the clamp can be manufactured from metals, ceramics, polymers, or any combination thereof. For instance, the clamp member 102, the clamp member 104, the lever 106, and the heads 108 can be manufactured out of a surgical grade stainless steel. In addition, clamp member 102 or the clamp member 104 can define a recess for receiving a polymer or ceramic insert (not shown) that can act as a gripping surface.

Figure 3:
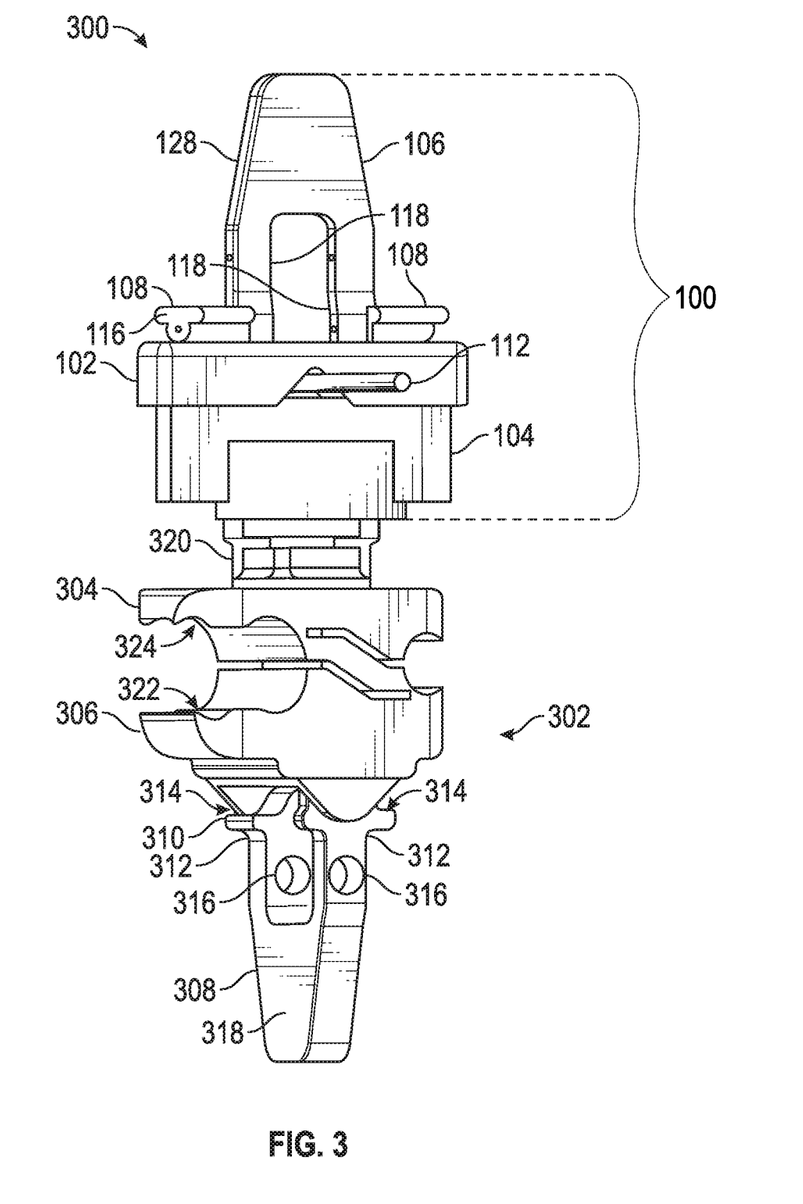
FIG. 3 shows an example of a clamping system consistent with embodiments disclosed herein.

FIG. 3 shows a clamping system 300. The clamping system 300 can include the clamp 100 (as shown in FIG. 1) and a clamp 302. The clamp 302 can include a clamp member 304, a clamp member 306, a lever 308, and a head 310. As shown in FIG. 3, the head 310 can be located in between cams 312. The head 310 can include recesses 314. The lever 308 can define locking holes 316.

The lever 308 can include a textured surface 318 and the cams 312 can include textured surfaces as described above with regards to FIGS. 1, 2A, and 2B. In addition, the lever 312 can pivot about a pivot axis provided by the head 310. The pivoting movement of the lever 308 can cause a distance between the clamp member 304 and the clamp member 306 to increase or decrease.

The clamp 100 and the clamp 302 can be connected by a rotational joint 320. The rotational joint 320 can allow the clamp 100 and the clamp 302 to rotate independently of one another. The rotational joint 320 can allow for the incremental positioning of the clamp 100 and the clamp 302 relative to one another. For example, the rotational joint 329 can allow the clamp 100 to move in 5 degree increments with respect to the clamp 302. Corresponding surfaces of the clamp 100 and the clamp 302 can have teeth that can be used to hold the clamp 100 and the clamp 302 in position relative to one another. When the cam 318 on the clamp body 302 is engaged, the cam 318 can cause components of the clamping system 300 close a gap between the clamp 100 and the clamp 302 and lock into place, The clamp member 304 and the clamp member 306 each can include gripping surfaces 322 and 324. The gripping surfaces 322 and 324 can be contoured to receive a rod, pin, or wire of a predetermined gauge or diameter. In addition, the size rod, pin, or wire received by the clamp 100 and the clamp 302 can be different sizes and diameters.

Just as with the clamp 100, the clamp 302 can be manufactured from a variety of materials and a variety of methods. For example, the clamp 302 can be manufactured from a surgical grade stainless steel and machined using a computer numerical controlled (CNC) milling machine. Other materials include, but are not limited to, polymers, ceramics, and any combination thereof. Other manufacturing techniques include, but are not limited to, injection molding, casting, and any combination thereof.

Figure 4:
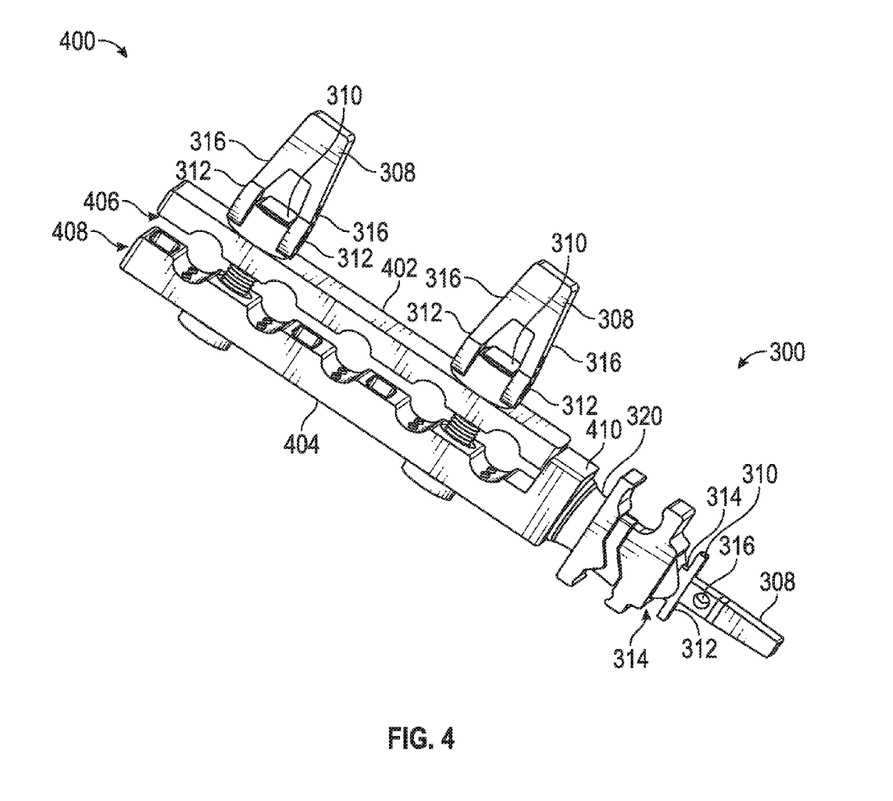
FIG. 4 shows an example of a clamp consistent with embodiments disclosed herein.

FIG. 4 shows a clamp 400. As shown in FIG. 4, the clamp 400 can include a clamp member 402 and a clamp member 404. The damp member 402 can define a plurality of gripping surfaces 406 and the clamp member 404 can define a plurality of gripping surfaces 408. The clamp members 402 and 404 can define any number of gripping surfaces sized to receive rods, pins, or wires having the same or different sizes. For example, as shown in FIG. 4, the plurality of gripping surfaces 406 and 408 can define five gripping surfaces having the same size, The clamp 400 can include a plurality of levers 308, and heads 310. The levers 308 attached to the clamp member 402 can be attached to the clamp member 402 with an adhesive or bolted as shown in FIGS. 1-3. During use, pivoting one of the levers 308 can cause a portion of the clamp member 402 to move in a direction towards a portion of the clamp member 404. The levers 308 can be secured in position using the recesses 314, locking holes 316, and locking pins as describe above with respect to FIGS. 1-3.

The clamp member 404 can also define an offset 410. The offset 410 can be used to secure a clamp, such as the clamp 302, to the clamp 400. For example, and as shown in FIG. 4, a rotational joint (such as the rotational joint 320) can be used to secure the clamp 302 to the offset 410.

As disclosed herein, the clamp 400 can be manufactured from a variety of materials and a variety of methods. For example, the clamp 400 can be manufactured from a surgical grade stainless steel and machined using a computer numerical controlled (CNC) milling machine. Other materials include, but are not limited to, polymers, ceramics, and any combination thereof. Other manufacturing techniques include, but are not limited to, injection molding, casting, and any combination thereof.

Figure 5:
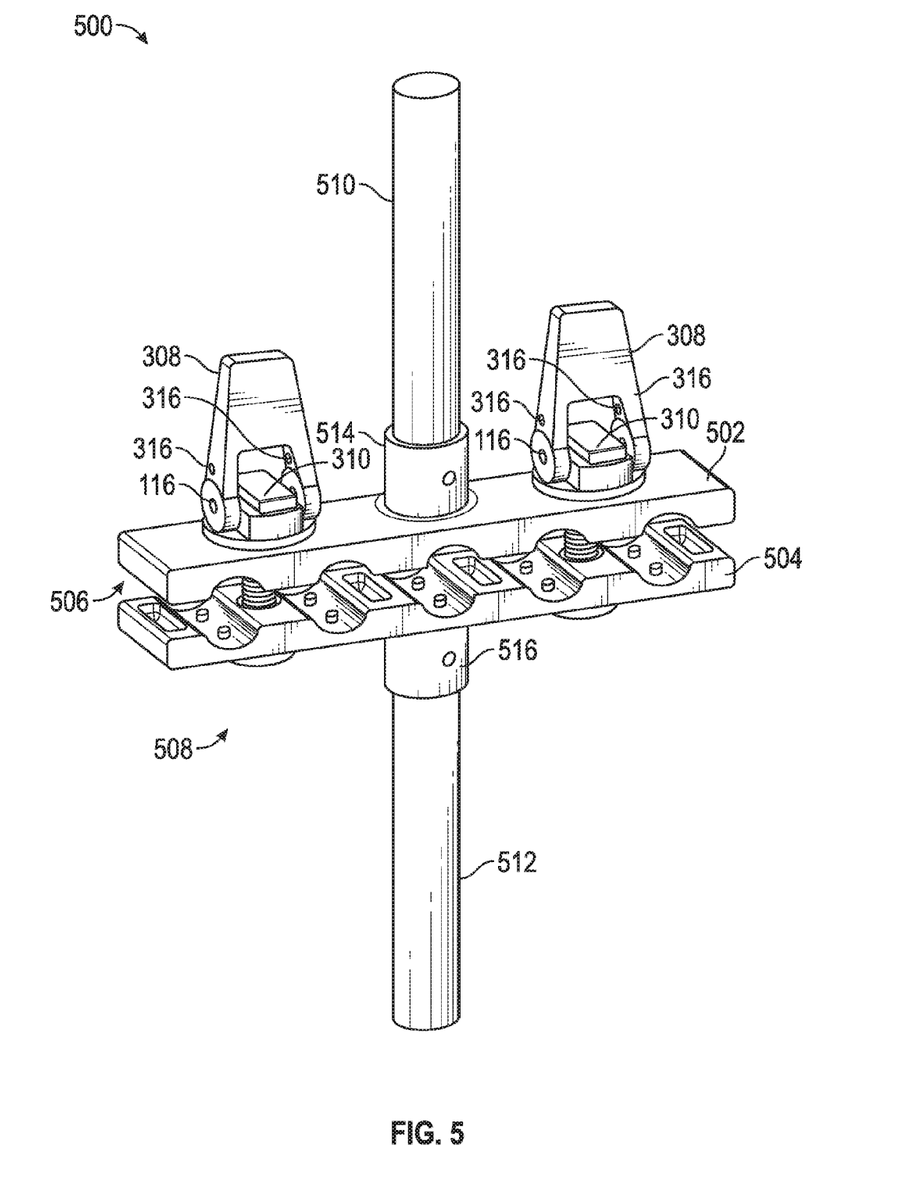
FIG. 5 shows an example of a clamp consistent with embodiments disclosed herein.

FIG. 5 shows a clamp 500. As shown in FIG. 5, the clamp 500 can include a clamp member 502 and a clamp member 504. The clamp member 502 can define a plurality of gripping surfaces 506 and the clamp member 504 can define a plurality of gripping surfaces 508. The clamp members 502 and 504 can define any number of gripping surfaces sized to receive rods, pins, or wires of the same or different sizes. For example, as shown in FIG. 5, the plurality of gripping surfaces 506 and 508 can define five gripping surfaces.

As shown in FIG. 5, a rod or pin 510 can be connected to the clamp member 502 and a rod or pin 512 can be connected to the clamp member 504. The clamp member 502 can define a connector 514 and the eight clamp member 504 can define a connector 516. The connector 514 and the connector 516 can be sized to receive the rod or pin 510 and the rod or pin 512, respectively. A set screw 518 and a set screw 520 can be used to secure the rod or pin 510 and the rod or pin 512, respectively, in position.

The clamp 500 can include a plurality of levers 308, and heads 310. The levers 308 attached to the clamp member 502 can be attached to the clamp member 502 with an adhesive or bolted as shown in FIGS. 1-3. During use, pivoting one of the levers 308 can cause a portion of the clamp member 502 to move in a direction towards a portion of the clamp member 504. The levers 308 can be secured in position using the recesses 314, locking holes 316, and locking pins as describe above with respect to FIGS. 1-3.

As disclosed herein, the clamp 500 can be manufactured from a variety of materials and a variety of methods. For example, the clamp 500 can be manufactured from a surgical grade stainless steel and machined using a computer numerical controlled (CNC) milling machine. Other materials include, but are not limited to, polymers, ceramics, and any combination thereof. Other manufacturing techniques include, but are not limited to, injection molding, casting, and any combination thereof.

Figure 6:
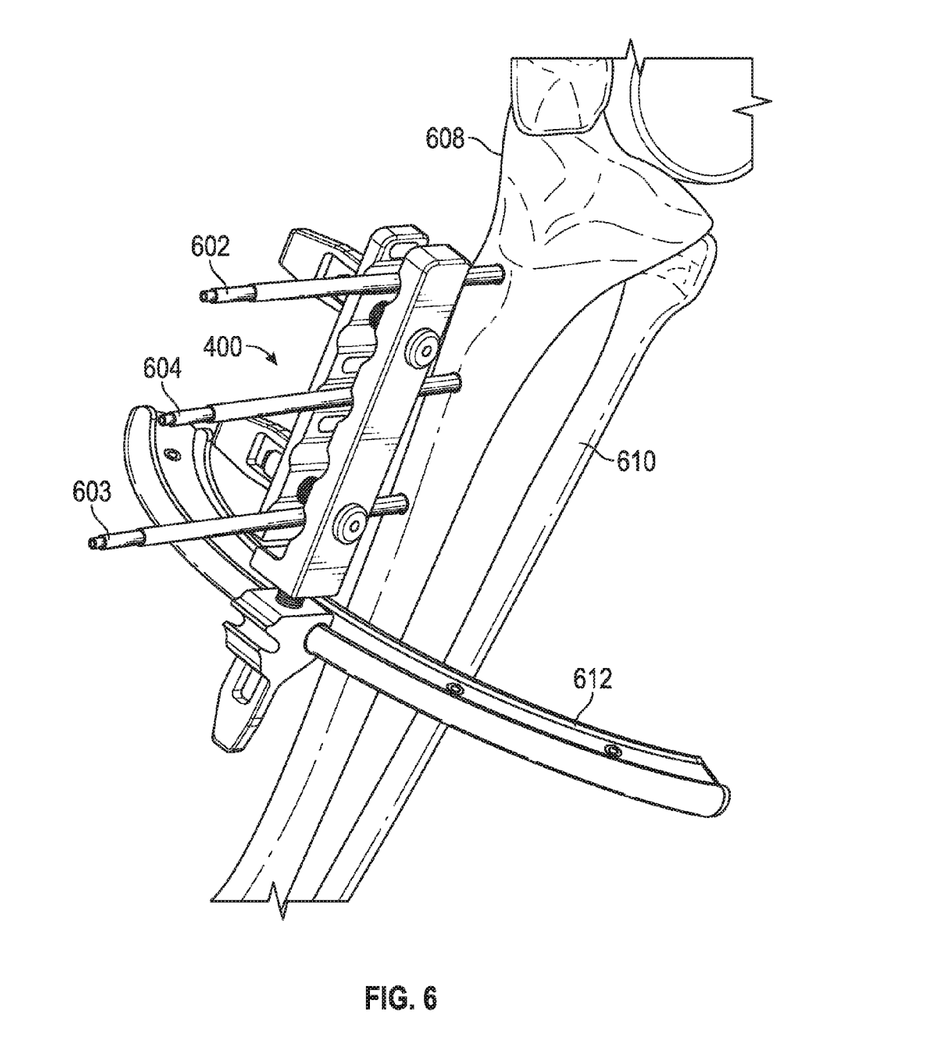
FIG. 6 shows an example clamping system consistent with embodiments disclosed herein.

FIG. 6 shows a clamping system 600. The clamping system 600 can include a plurality of pins, wires, or rods, such as a pin 602, a pin 604, and a pin 606. The plurality of pins, wires, or rods, can be connected to a bone, such as a tibia 608 or fibula 610. A clamp, such the clamp 400, can connect the plurality of pins, wires, or rods to a curved support 612, such as a component of an external fixation device such as a Ilizarov apparatus. While FIG. 6 shows the clamp 400, the clamping system 600 can include any combination of clamps disclosed herein.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. A clamping system comprising:
   a plurality of rods, wires, or pins; and
   a plurality of clamps, each of the plurality of clamps including:
      a first clamp member including a first gripping surface,
      a second clamp member including a second gripping surface, and
      a lever connected to the first clamp member, the lever defining a cam located proximate the first clamp member, the lever pivotable between a first position, a second position, and a third position,
   wherein the first position includes a first portion of the cam contacting the first clamp member, the second position includes a second portion of the cam contacting the first clamp member, and the third position include a third portion of the cam contacting the first clamp member, the second portion of the cam opposite the third portion of the cam,
   wherein a transition from the first position to the second position or the third position causes the cam to move the second clamp member towards the first clamp member such that the second portion of the cam or the third portion of the cam contacts the first clamp member, respectively,
   wherein each of the plurality of clamps is sized to clamp onto at least one of the plurality of rods, wires, or pins.

2. The clamp of claim 1, wherein each of the plurality of clamps further comprises:
   a head connecting the lever to the first clamp member, the head providing a pivot axis about which the lever pivots; and
   a locking pin,
   wherein the head defines a recess and the lever defines a locking hole,
   wherein when the lever is in the second position, the locking hole is aligned with the recess such that the locking pin fits into the locking hole and the recess.

3. The clamp of claim 1, wherein the first gripping surface of one of the plurality of clamps defines a notch sized to receive a predetermined gauge wire.

4. The clamp of claim 1, wherein at least one of the first clamp member and the second clamp member of one of the plurality of clamps includes a textured gripping surface.

5. The clamp of claim 1, wherein when the lever of one of the plurality of clamps is in the second position, the first gripping surface and the second gripping surface of the one of the plurality of clamps exert a predetermined gripping force on one of the plurality of rods, wires, or pins.

6. The clamp of claim 1, further comprising a second clamp connected to one of the plurality of clamps.

7. The clamp of claim 6, further comprising a rotational joint connecting the one of the plurality of clamps to the second clamp, wherein the rotational joint allows the second clamp to rotate independently of the one of the plurality of clamps.

8. The clamp of claim 6, wherein the second clamp includes a third gripping surface defined by the first clamp member of the one of the plurality of clamps and a fourth gripping surface defined by the second clamp member of the one of the plurality of clamps.

9. The clamp of claim 6, wherein the one of the plurality of clamps is sized to grip a first rod, wire, or pin of the plurality of rods, wires, or pins and the second clamp is sized to grip a second rod, wire, or pin of the plurality of rods, wires or pins, the first rod, wire, or pin and the second rod, wire, or pin being of different gauges.

10. The damping system of claim 1 wherein at least one of the plurality of clamps is sized to clamp onto at least two of the plurality of rods, wires, or pins.

11. The clamping system of claim 1, wherein each of the plurality of rods, wires, or pins are of different gauges.

12. The clamping system of claim 1, further comprising a curved support, at least one of the plurality of clamps sized to connect to the curved support.

* * * * *

UNITED STATES PATENT AND TRADEMARK OFFICE
CERTIFICATE OF CORRECTION

| | |
|---|---|
| PATENT NO. | : 10,172,646 B2 |
| APPLICATION NO. | : 14/991257 |
| DATED | : January 8, 2019 |
| INVENTOR(S) | : Slagle |

Page 1 of 1

It is certified that error appears in the above-identified patent and that said Letters Patent is hereby corrected as shown below:

On the Title Page

On page 2, in Column 1, item (56) under "Other Publications", Line 3, delete "Reponse" and insert --Response-- therefor In the Claims In Column 8, Line 45, in Claim 10, delete "damping" and insert --clamping-- therefor Signed and Sealed this
Fourteenth Day of April, 2020

Andrei Iancu
*Director of the United States Patent and Trademark Office*